(12) United States Patent
Qiu et al.

(10) Patent No.: US 11,110,033 B2
(45) Date of Patent: Sep. 7, 2021

(54) INTEGRATED STRUCTURE OF PREPARATION SYRINGE

(71) Applicant: JIANGNAN UNIVERSITY, Jiangsu (CN)

(72) Inventors: Yuyu Qiu, Jiangsu (CN); Jun Wang, Jiangsu (CN); Shufang Xia, Jiangsu (CN); Yuyu Jiang, Jiangsu (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 472 days.

(21) Appl. No.: 16/303,656

(22) PCT Filed: Dec. 26, 2017

(86) PCT No.: PCT/CN2017/118535
§ 371 (c)(1),
(2) Date: Nov. 20, 2018

(87) PCT Pub. No.: WO2019/126992
PCT Pub. Date: Jul. 4, 2019

(65) Prior Publication Data
US 2020/0093693 A1 Mar. 26, 2020

(30) Foreign Application Priority Data
Dec. 25, 2017 (CN) .......................... 201711421735.1

(51) Int. Cl.
*A61J 1/20* (2006.01)
*A61J 1/14* (2006.01)
(Continued)

(52) U.S. Cl.
CPC .......... *A61J 1/2096* (2013.01); *A61J 1/1406* (2013.01); *A61J 1/18* (2013.01); *A61J 1/201* (2015.05);
(Continued)

(58) Field of Classification Search
CPC ........ A61M 2005/31518; A61M 5/288; A61M 5/345; A61M 5/178; A61M 5/315;
(Continued)

(56) References Cited

U.S. PATENT DOCUMENTS 3,498,295 A 3/1970 Brickson et al.
3,545,607 A * 12/1970 Keller ..................... A61M 5/28
206/365
(Continued)

FOREIGN PATENT DOCUMENTS

| CN | 2899809 | 5/2007 |
| CN | 200984372 | 12/2007 |
| CN | 104132038 | 11/2014 |

OTHER PUBLICATIONS

"International Search Report (Form PCT/ISA/210)", dated Apr. 23, 2018, pp. 1-5.

*Primary Examiner* — Ariana Zimbouski
(74) *Attorney, Agent, or Firm* — JCIPRNET

(57) ABSTRACT

An integrated structure of a preparation syringe includes a stretchable piston, a barrel, a needle, an exposed rubber plug, a sealing sheet, a built-in rubber plug, a sealing rubber plug and an engaging rubber plug. One end of the barrel is provided with the stretchable piston, and another end of the barrel is provided with a clamping column. The exposed rubber plug is provided on a side of the stretchable piston away from the barrel. The built-in rubber plug is provided within the barrel. A Scale mark is provided on a circumferential surface of the barrel. The sealing rubber plug is inlaid and sleeved on the clamping column. The sealing sheet is provided on a side of exposed tuber plug away from the barrel. A blunt end is provided at an end of the needle away form a needle tip. The engaging rubber plug is provided outside the blunt end.

6 Claims, 3 Drawing Sheets

(51) Int. Cl.
  *A61J 1/18*   (2006.01)
  *A61M 5/28*   (2006.01)
  *A61M 5/34*   (2006.01)
  *A61M 5/315*  (2006.01)

(52) U.S. Cl.
  CPC ............ *A61J 1/2041* (2015.05); *A61M 5/288* (2013.01); *A61M 5/345* (2013.01); *A61J 2205/50* (2013.01); *A61M 2005/31518* (2013.01)

(58) Field of Classification Search
  CPC ........ A61J 1/2096; A61J 1/201; A61J 1/2041; A61J 1/1406; A61J 1/18; A61J 2205/50
  See application file for complete search history.

(56) References Cited

U.S. PATENT DOCUMENTS

| | | | |
|---|---|---|---|
| 3,916,893 A | 11/1975 | De Felice | |
| 2009/0259195 A1 | 10/2009 | Lin Lee | |
| 2013/0304021 A1* | 11/2013 | Cabiri | A61M 5/31511 604/506 |
| 2013/0338575 A1* | 12/2013 | Glocker | A61M 5/286 604/57 |
| 2018/0326159 A1* | 11/2018 | Wendland | A61M 5/2033 |

* cited by examiner

INTEGRATED STRUCTURE OF PREPARATION SYRINGE

CROSS-REFERENCE TO RELATED APPLICATION

This is a 371 application of the International PCT application serial no. PCT/CN2017/118535, filed on Dec. 26, 2017, which claims the priority benefits of China Application No. 201711421735.1, filed on Dec. 25, 2017. The entirety of each of the above-mentioned patent applications is hereby incorporated by reference herein and made a part of this specification.

TECHNICAL FIELD OF THE INVENTION

The present invention belongs to the technical field of syringes, and in particular, to a preparation syringe with an integrated structure.

BACKGROUND

It is a common clinical medical behavior to perform various injection treatments after preparing liquid medicine through a sealed bottle. The medicine in the sealed bottle is usually provided with a liquid agent or a powder injection agent. The powder injection agent is more common, and needs to be dissolved into a liquid form by a solvent and is used after being aspirated by a syringe.

SUMMARY

Technical Problem

In the process of aspirating and injecting liquid medicine with a conventional syringe, there are mainly following problems. First, waste of liquid medicine, which is mainly caused due to the following factors: liquid medicine extravasation. When the liquid medicine is aspirated, the liquid medicine can overflow from the needle due to increase of the pressure inside the sealed bottle, at the same time, the overflown liquid can form toxic particulate aerosols or aerosols invisible by naked eyes, which causes harm to medical personnel through skin, respiratory tract, or other means, and causes pollution to the environment. Aspiration inadequacy of the liquid medicine is caused due to a special structure of the sealed bottle. Wall-hanging infusion droplets and liquid medicine remaining in a sealing ring of a bottle opening cannot be sucked out. The liquid medicine fails to be injected completely, so that part of the liquid medicine remains in needle plug when using a conventional syringe. Second, increase in possibility of bacterial contamination. Powder injection agent usually requires the syringe to enter and exit twice to dissolve and aspirate the medicine, such process increases the possibility of contamination of the liquid medicine and the syringe. Third, invasion of infusion particles, because the sealing ring of the sealed bottle is made of rubber-like material, repeated punctures may cause the particles to enter the liquid medicine, thereby causing potential harm to the patient. Fourth, repeated dissolution and aspiration of the liquid medicine takes time and labor during the preparation of the liquid medicine.

Technical Solution

An integrated structure of a preparation syringe includes a stretchable piston, a barrel, a needle, an exposed rubber plug, a sealing sheet, a built-in rubber plug, a sealing rubber plug, and an engaging rubber plug. One end of the barrel is provided with the stretchable piston, and another end of the barrel is provided with a clamping column. The exposed rubber plug is provided on the side of the stretchable piston away from the barrel. The built-in rubber plug is provided within the barrel. A scale mark is provided on a circumferential surface of the barrel. The sealing rubber plug is inlaid and sleeved on the clamping column. The sealing sheet is provided on a side of exposed rubber plug away from the barrel. A blunt end is provided at an end of the needle away from a needle tip. The engaging rubber plug is provided outside the blunt end.

Preferably, the stretchable piston includes a multi-layer hollow sleeve consisting of a plurality of hollow sleeves that are sequentially reduced in diameter. Adjacent hollow sleeves are engaged with each other through a clamping groove and a protrusion. After an inner-layer hollow sleeve is pulled out of an outer-layer hollow sleeve and the protrusion is located in the clamping groove, the inner-layer hollow sleeve is fixed relative to the outer-layer hollow sleeve.

Preferably, the exposed rubber plug is connected to the built-in rubber plug through a connecting rod. The connecting rod has a hollow structure therein.

Preferably, the engaging rubber plug has an E-shaped structure in cross section.

Preferably, the needle is inlaid and sleeved on the clamping column through the engaging rubber plug.

Preferably, the sealing sheet is provided outside both the exposed rubber plug and the sealing rubber plug.

Preferably, a through-hole is provided inside the clamping column.

Advantageous Effect

In the present invention, a storage vial and a syringe are designed to be an integrated structure, and it is a wholly new design with a novel structure. When in use, an intermediate link is reduced, so as to reduce the waste of liquid medicine caused by the aspiration inadequacy of the liquid medicine and the overflow of liquid medicine, and at the same time reduce the occupational risk of the medical personnel and reduce potential harm to the patient due to particles caused by repeated punctures. The matching design of the stretchable piston structure reduces the overall length, and facilitates puncture operations. The adoption of a needle with an E-shaped structure in cross section also effectively avoids the waste of liquid medicine.

DETAILED DESCRIPTION OF THE INVENTION

The technical solutions in the embodiments of the present invention are hereinafter described clearly and completely with reference to the accompanying drawings in the embodiments of the present invention. Obviously, the embodiments described here are part of the embodiments of the invention and not all of the embodiments. All other embodiments, which can be derived by persons skilled in the art from the embodiments given herein without creative efforts, shall fall within the protection scope of the present invention.

Figure 1:
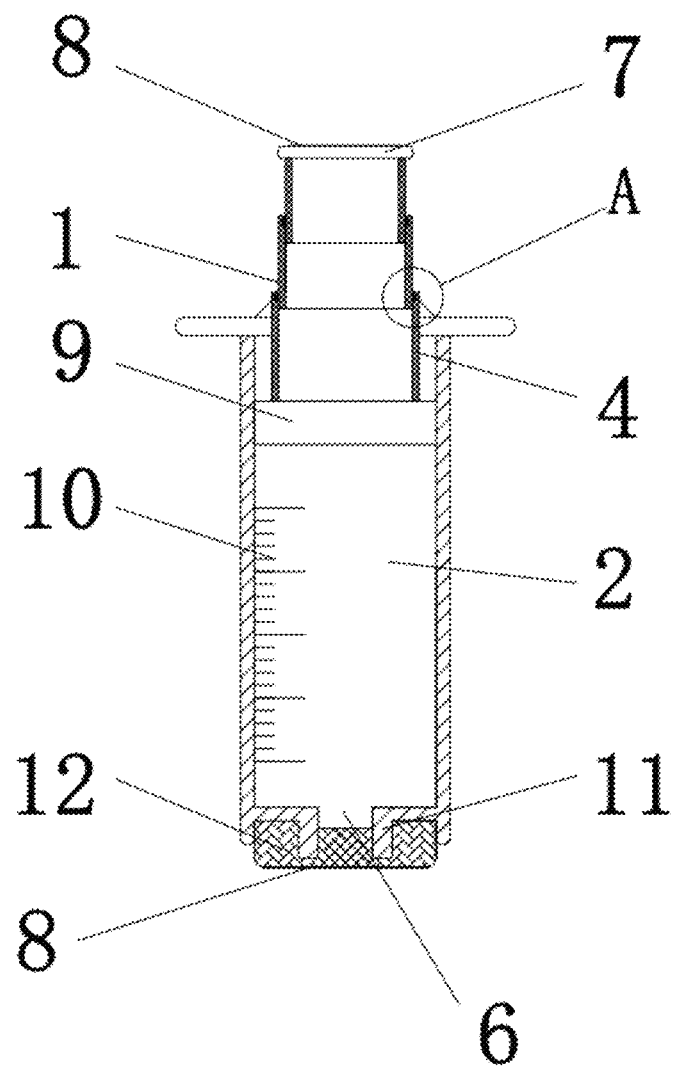
FIG. 1 is a schematic structural diagram according to the present invention.
Figure 2:
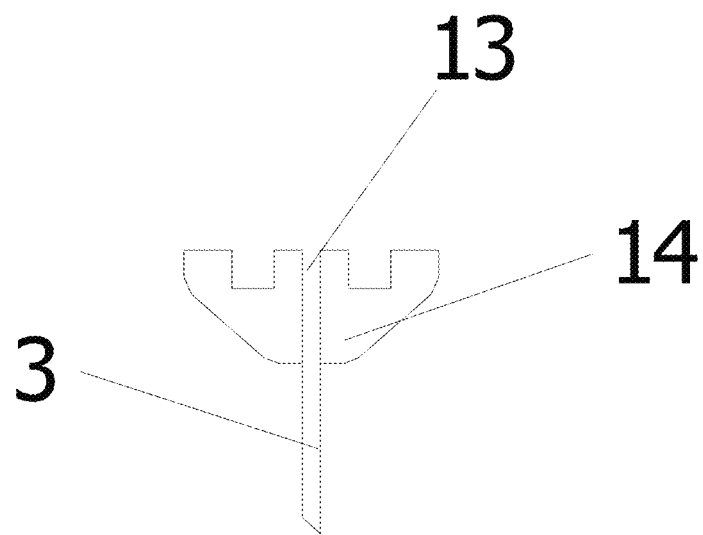
FIG. 2 is a schematic structural diagram of a needle according to the present invention.
Figure 3:
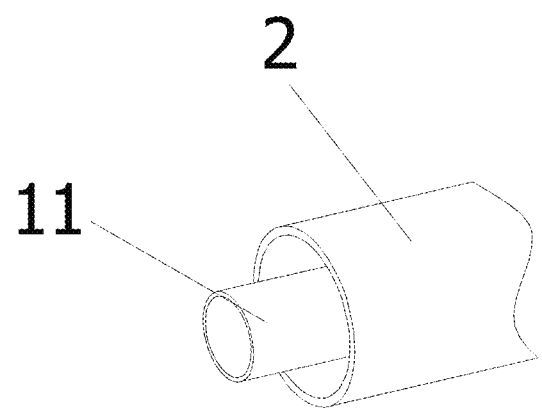
FIG. 3 is a schematic structural diagram of a head end of a barrel according to the present invention.
Figure 4:
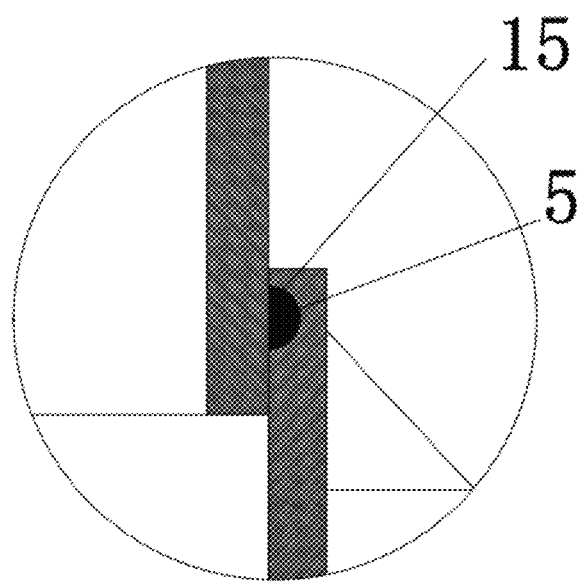
FIG. 4 is a partially enlarged view of region A in FIG. 1.

Please refer to FIG. 1 to FIG. 4, the present invention provides following technical solutions. An integrated structure of a preparation syringe includes a stretchable piston 1, a barrel 2, a needle 3, an exposed rubber plug 7, a sealing sheet 8, a built-in rubber plug 9, a sealing rubber plug 12 and an engaging rubber plug 14. One end of the barrel 2 is provided with the stretchable piston 1, and another end of the barrel 2 is provided with a clamping column 11. The stretchable piston 1 includes a multi-layer hollow sleeve 4 consisting of several hollow sleeves being sequentially reduced in diameter and a clamping groove 5. Adjacent hollow sleeves are engaged with each other through a clamping groove 5 and an elastic protrusion 15. The elastic protrusion 15 further functions as a sealing ring. After the multi-layer hollow sleeve 4 is pulled apart, the clamping groove 5 is engaged with the protrusion 15 to fix the multi-layer hollow sleeve. After the elastic protrusion 15 engages the clamping groove 5, the exposed rubber plug 7 is provided on a side of the stretchable piston 1 away from the barrel 2. The built-in rubber plug 9 is provided within the barrel 2. That is, a lower end of the outermost hollow sleeve is connected to the built-in rubber plug 9, and an upper end of the innermost hollow sleeve is connected to the exposed rubber plug 7. A scale mark 10 is provided on a circumferential surface of the barrel 2. The sealing rubber plug 12 is inlaid and sleeved on the clamping column 11. An opening of the clamping column 11 is sealed by the sealing rubber plug 12. The sealing sheet 8 is provided outside both the exposed rubber plug 7 and the sealing rubber plug 12. The sealing sheet 8 is provided on a side of exposed rubber plug 7 away from the barrel 2. A blunt end 13 is provided at an end of the needle 3 away from the needle tip. The engaging rubber plug 14 is provided outside the blunt end 13. The engaging rubber plug 14 has an E-shaped structure in cross section. The needle 3 is inlaid and sleeved on the clamping column 11 through the engaging rubber plug 14. A through-hole 6 is provided inside the clamping column 11.

The working principle and the use process of the present invention are as follows.

When in use, the barrel 2 and the expandable piston 1 are an assembly structure to form a sealing device, which a liquid-form medicine or a powder injection agent medicine can be accommodated therein. In the case of the liquid-form medicine, when in use, let the clamping column 11 of the barrel 2 face upwards, reveal the sealing sheet 8, remove the sealing rubber plug 12, insert the blunt end 13 of the needle 3 into the clamping column 11, and pull open the stretchable piston 1. When a snap sound is heard (the clamping groove 5 is matched with the protrusion 15), fix the piston (the inner and the outer hollow sleeves are fixed relatively to each other, after being stretched, the multi-layer hollow sleeve is relative to the push rod of the built-in rubber plug 9), gently push the piston to exhaust air, perform an injection operation according to the conventional method, so that the built-in rubber plug 9 can completely in tight contact with a bottom of the syringe barrel 2 to complete the injection. In the case of a powder injection agent medicine, when in use, first, reveal the rubber plug sealing sheet 8 at an exposed end of the piston for sterilization, puncture aspirated solvent into the exposed piston through another conventional syringe needle. The needle arrives at a built-in piston via a hollow part of the piston hollow sleeve and penetrates through the built-in piston to inject the solvent into the barrel 2, and pull out the conventional syringe needle to fully dissolve the medicine into a solution form. Face the clamping column 11 of the barrel 2 upwards, reveal the sealing sheet 8, remove the sealing rubber plug 12, engage the blunt end 13 of the needle 3 with the clamping column 11, and pull open the stretchable piston 1. When a snap sound is heard, fix the piston, gently push the piston to exhaust air, perform an injection operation according to the conventional method, so that the built-in rubber plug 9 can completely in tight contact with the bottom of the syringe barrel 2 to complete the injection.

In the present invention, the positioning and engaging structure matched between the inner and outer adjacent hollow sleeves is not limited to the clamping groove 5 and the protrusion 15 in the above embodiments; other structures which can achieve a relative fixing effect of the inner and outer sleeves after stretching are also possible.

While embodiments have been shown and described, it will be understood by persons skilled in the art that various alterations, modifications, replacements or variations may be made to these embodiments without departing from the principle and spirit of the present invention, and the scope of the present invention should be limited by the appended claims and their equivalents.

What is claimed is:

1. A preparation syringe system, comprising a stretchable piston, a barrel, a needle, an exposed rubber plug, a first sealing sheet, a second sealing sheet, a built-in rubber plug, a sealing rubber plug, and an engaging rubber plug, wherein the stretchable piston, the barrel, the exposed rubber plug, the first sealing sheet, and the built-in rubber plug form an integrated structure, wherein one end of the barrel is provided with the stretchable piston, another end of the barrel is provided with a clamping column, the exposed rubber plug is provided on a side of the stretchable piston away from the barrel, the built-in rubber plug is provided inside the barrel, a scale mark is provided on a circumferential surface of the barrel, the sealing rubber plug is removably inlaid and sleeved on the clamping column, the first sealing sheet is provided on a side of the exposed rubber plug away from the barrel, a blunt end is provided at an end of the needle away from a needle tip, and the engaging rubber plug is provided outside the blunt end, wherein the second sealing sheet is provided outside the sealing rubber plug, when the second sealing sheet is revealed and the sealing rubber plug is removed from the clamping column of the barrel, the needle is able to be assembled on the integrated structure through the engaging rubber plug.

2. The preparation syringe system according to claim 1, wherein the stretchable piston comprises a multi-layer hollow sleeve consisting of a plurality of hollow sleeves that are sequentially reduced in diameter, adjacent hollow sleeves are engaged with each other through a clamping groove and a protrusion, after an inner-layer hollow sleeve is pulled out of an outer-layer hollow sleeve and the protrusion is located in the clamping groove, the inner-layer hollow sleeve is fixed relative to the outer-layer hollow sleeve.

3. The preparation syringe system according to claim 1, wherein the engaging rubber plug has an E-shaped structure in cross section.

4. The preparation syringe system according to claim 1, wherein the needle is inlaid and sleeved on the clamping column through the engaging rubber plug.

5. The preparation syringe system according to claim 1, wherein the first sealing sheet is provided outside the exposed rubber plug.

6. The preparation syringe system according to claim 1, wherein a through-hole is provided inside the clamping column.

* * * * *